United States Patent [19]

Iwasaki

[11] 4,212,970

[45] Jul. 15, 1980

[54] 2-HALOMETHYL-5-VINYL-1,3,4-OXADIAZOLE COMPOUNDS

[75] Inventor: Masayuki Iwasaki, Minami-ashigara, Japan

[73] Assignee: Fuji Photo Film Co., Ltd., Minami-ashigara, Japan

[21] Appl. No.: 962,851

[22] Filed: Nov. 22, 1978

[30] Foreign Application Priority Data

Nov. 28, 1977 [JP] Japan ............................ 52-142473
Aug. 8, 1978 [JP] Japan ............................ 53-96306

[51] Int. Cl.$^2$ ................. C07D 271/10; C07D 407/02
[52] U.S. Cl. ................... 542/455; 430/925; 542/456; 542/457; 542/458
[58] Field of Search .............. 542/455, 456, 457, 458

[56] References Cited

U.S. PATENT DOCUMENTS

| 3,954,475 | 5/1976 | Bonham et al. | 542/457 |
| 3,987,037 | 10/1976 | Bonham et al. | 542/457 |

FOREIGN PATENT DOCUMENTS

| 2047465 | 3/1972 | Fed. Rep. of Germany | 542/457 |
| 2073992 | 10/1971 | France | 542/457 |

*Primary Examiner*—Arthur P. Demers
*Attorney, Agent, or Firm*—Sughrue, Rothwell, Mion, Zinn & Macpeak

[57] ABSTRACT

Compounds represented by the following general formula:

$$W-CH=C(X)-\underset{O}{\underset{|}{C}}\underset{\diagdown}{\overset{N-N}{\diagup}}C-CH_{3-n}Y_n$$

wherein W represents a phenyl group, a phenyl group substituted with a member selected from the group consisting of a halogen atom, a nitro group, a cyano group, an alkyl group containing 1 to 3 carbon atoms and an alkoxy group containing 1 to 4 carbon atoms, with the number of the substituents being 1 or 2 when said substituent is a halogen atom and 1 when said substituent is other than halogen, or an unsubstituted naphthyl group, and said phenyl group may take the form of $$H_2C\underset{O}{\overset{O}{<}}\text{(benzo-fused)}$$

X represents a hydrogen atom, an unsubstituted phenyl group or an alkyl group containing 1 to 3 carbon atoms, Y represents a halogen atom, and n represents an integer of 1 to 3. These compounds are useful as photo-initiators.

11 Claims, No Drawings

2-HALOMETHYL-5-VINYL-1,3,4-OXADIAZOLE COMPOUNDS

BACKGROUND OF THE INVENTION

1. Field of the Invention

The present invention relates to novel 2-halomethyl-5-vinyl-1,3,4-oxadiazole compounds.

2. Brief Discussion of the Prior Art

Compounds capable of being decomposed upon exposure to light to form free radicals (free radical-generating agents) are well known in the field of graphic arts. They are widely used as photo-polymerization initiators in photo-polymerizable compositions, as a light-activatable agents in free radical photographic compositions, and as a photo-initiators for the reaction catalyzed by an acid generated by light. Various light-sensitive materials useful in image-forming systems such as printing, copying, and the like are prepared using such free radical-generating agents.

Organic halogen compounds release halogen free radicals when exposed to light, and, hence, they are useful as photo-initiators. As this type of organic halogen compounds, carbon tetrabromide, iodoform, tribromoacetophenone, etc., are typical and have widely been used. However, these free radical-generating agents have the defect that they are only decomposed by light of considerably limited wavelength region. That is, they respond to light in ultraviolet region wavelength which is shorter than the main wavelength of light emitted from ordinarily used light sources. Therefore, these compounds fail to effectively utilize light in near ultraviolet to visible region emitted from such light sources, thus, being poor in free radical-generating ability.

SUMMARY OF THE INVENTION

A principle object of the present invention is to provide a novel free radical generating photo-initiator.

Another object of the present invention is to provide a photo-initiator useful for a light-sensitive composition which gives, upon exposure to actinic light, visible images without development.

Still a further object of the present invention is to provide a photo-initiator suitable for a photosensitive composition which enables one to obtain images visible under a yellow safety lamp by exposure only such that it is possible to know whether a plate coated with the photosensitive composition containing the photo-initiator of the present invention has been exposed.

A further object of the present invention is to provide a novel compound which is responsive to light over a fairly broad wavelength region.

These and other objects of the present invention are accomplished with the compounds described below in detail.

DETAILED DESCRIPTION OF THE INVENTION

Novel compounds represented by the following general formula (I) have now been found to be useful as materials capable of removing the above-described defect and showing excellent free radical-generating ability with high sensitivity to light:

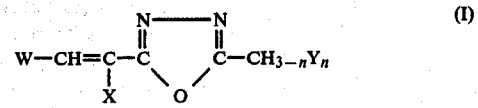

In the above formula, W represents a substituted or unsubstituted phenyl group, or an unsubstituted naphthyl group, the phenyl group substituents are a halogen atom (e.g., chlorine, bromine, fluorine, etc.), a nitro group, a cyano group, an alkyl group containing 1 to 3 carbon atoms (e.g., methyl, ethyl, propyl, etc.) or an alkoxy group containing 1 to 4 carbon atoms (e.g., methoxy, ethoxy, butoxy, etc.), said substituted phenyl group may take the form of

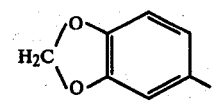

and of the groups for W, an unsubstituted phenyl or naphthyl group, a phenyl group substituted with one chlorine atom or an alkoxy group having 1 to 4 carbon atoms, and a group represented by the following formula

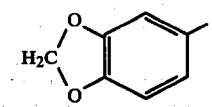

are preferred. The number of substituents in the phenyl group is 1 or 2 when a halogen atom is the substituent, or 1 when another substituent is the substituent, X represents a hydrogen atom, an alkyl group containing 1 to 3 carbon atoms (e.g., methyl, etc.) or an unsubstituted phenyl group, and of these groups, hydrogen atom is preferred. Y represents a halogen atom (e.g., chlorine, bromine or fluorine, preferably chlorine or bromine and most preferably chlorine), and n represents an integer of 1 to 3.

The novel 2-halomethyl-5-vinyl-1,3,4-oxadiazoles of the present invention can be advantageously synthesized according to a series of the reactions illustrated by the following reaction formulae:

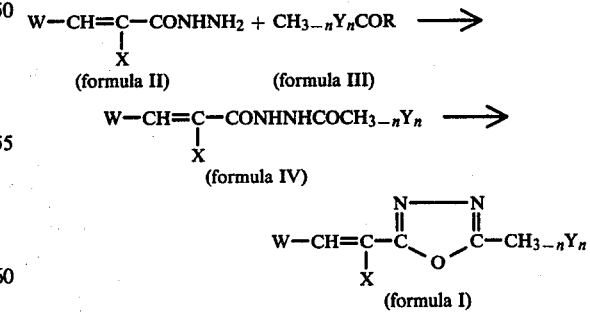

In the above formulae, W, X, Y and n are the same as defined in general formula (I), and R represents a trichloromethyl group, $-O-CO-CH_{3-n}Y_n$, a fluorine atom, a chlorine atom or a bromine atom.

Of the acrylic acid hydrazine derivatives of general formula (II) to be used for preparing the compounds of the present invention, cinnamic acid hydrazide, p-nitrocinnamic acid hydrazide, p-cyanocinnamic acid hydrazide, 2,4-dichlorocinnamic acid hydrazide, p-chlorocinnamic acid hydrazide, p-methylcinnamic acid hydrazide, p-methoxycinnamic acid hydrazide, m-methoxycinnamic acid hydrazide, o-methoxycinnamic acid hydrazide, p-n-butoxycinnamic acid hydrazide, 3,4-methylenedioxycinnamic acid hydrazide, naphthylacrylic acid hydrazide, α-methylcinnamic acid hydrazide, α-phenylcinnamic acid hydrazide, etc., are preferable. These acrylic acid hydrazide derivatives can be synthesized according to the processes described in W. O. Godtfredsen & S. Vangedal, *Acta Chem. Scand.*, 9, 1498 (1955) and S. Harada & H. Kondo, *Bull. Chem. Soc. Jap.*, 41, (10), 2521 (1968). That is, the synthesis is conducted by adding mixed-acid anhydride synthesized from an alkali metal salt of acrylic acid derivative and ethyl chlorocarbonate to an ice-cooled chloroform dispersion of hydrazine hydrate and allowing the reaction system to stand for one night at 0° C., or by dissolving or dispersing an activated ester of acrylic acid derivative such as cyanomethyl ester or p-nitrophenyl ester in methanol, chloroform, etc., adding hydrazine hydrate thereto, and stirring at a temperature of room temperature to reflux temperature. The thus-obtained crude acrylic acid hydrazides can be purified by recrystallization from ethanol, methanol or water.

Of the compounds of general formula (III) to be used in preparing the compounds of the present invention, hexachloroacetone, hexabromoacetone, trichloroacetic acid anhydride, dichloroacetic acid anhydride, monochloroacetic acid anhydride, tribromoacetic acid anhydride, dibromoacetic acid anhydride, monobromoacetic acid anhydride, trichloroacetic acid chloride, dichloroacetic acid chloride, monochloroacetic acid chloride, tribromoacetic acid bromide, dibromoacetic acid bromide, monobromoacetic acid chloride, monobromoacetic acid bromide, etc., are preferable.

Preparation of the compounds of general formula (IV) from the compound of general formula (II) and the compound of general formula (III) can be conducted according to known processes.

For example, there are a process of stirring the acrylic acid hydrazide derivative and a slightly excess amount of hexachloroacetone or hexabromoacetone in a solvent such as acetonitrile at a temperature of room temperature to reflux temperature; a process of stirring the acrylic acid hydrazide derivative together with an equimolar amount of haloacetic acid anhydride; and a process of stirring 2 moles of the acrylic acid hydrazide derivative with 1 mole of haloacetic acid halide at room temperature using a solvent such as dioxane or tetrahydrofuran. The thus-obtained crude product can be purified by recrystallization from acetonitrile, ethanol, methanol, or the like.

Conversion of the compound of general formula (IV) to corresponding 1,3,4-oxadiazole can be conducted according to the process described in M. P. Hutt, E. F. Elslager & L. M. Werbel, *J. Heterocyclic Chem.*, 7 (3), 511 (1970).

That is, 1,3,4-oxadiazoles can be synthesized by heating under reflux N-acryloyl-N'-haloacetylhydrazide compound together with 2-fold moles or more of phosphorus oxychloride, acetic acid anhydride or the like. Suitable examples of the solvent for the reaction include toluene, benzene, etc. The thus-obtained crude product can be purified by recrystallization from ethanol, aqueous ethanol, etc.

As the specific examples of the compounds of the present invention, there are those illustrated below.

| Compound | Structural Formula | m.p. (°C.) | MeOH $\lambda_{Max}$ | $\epsilon \times 10^{-4}$ |
|---|---|---|---|---|
| 1 | C₆H₅—CH=CH—C(=N-N=)C—CCl₃ (with O bridge) | 121–122 | 303 | 2.55 |
| 2 | O₂N—C₆H₄—CH=CH—C(=N-N=)C—CCl₃ (with O bridge) | 178–181 | 319 | 3.99 |
| 3 | NC—C₆H₄—CH=CH—C(=N-N=)C—CCl₃ (with O bridge) | 200–201.5 | 303 | 3.79 |
| 4 | 2,4-Cl₂-C₆H₃—CH=CH—C(=N-N=)C—CCl₃ (with O bridge) | 153–155 | 305 | 2.71 |
| 5 | Cl—C₆H₄—CH=CH—C(=N-N=)C—CCl₃ (with O bridge) | 161.5–163.5 | 311 | 3.31 |
| 6 | CH₃—C₆H₄—CH=CH—C(=N-N=)C—CCl₃ (with O bridge) | 172–173 | 315 | 3.28 |

-continued

| Compound | Structural Formula | m.p. (°C.) | MeOH $\lambda$Max | $\epsilon \times 10^{-4}$ |
|---|---|---|---|---|
| 7 | 4-CH₃O-C₆H₄-CH=CH-C(=N-N=)O-C-CCl₃ (1,3,4-oxadiazole) | 140.5-141.5 | 332 | 3.16 |
| 8 | 3-CH₃O-C₆H₄-CH=CH-C(=N-N=)O-C-CCl₃ | 99-101 | 301 | 2.62 |
| 9 | 2-CH₃O-C₆H₄-CH=CH-C(=N-N=)O-C-CCl₃ | 107.5-109 | 340 | 1.65 |
| 10 | 4-n-C₄H₉O-C₆H₄-CH=CH-C(=N-N=)O-C-CCl₃ | 117.5-119.5 | 335 | 3.21 |
| 11 | 3,4-methylenedioxy-C₆H₃-CH=CH-C(=N-N=)O-C-CCl₃ | 156-158 | 342 | 2.60 |
| 12 | 1-naphthyl-CH=CH-C(=N-N=)O-C-CCl₃ | 195-205 | 330 | 1.48 |
| 13 | C₆H₅-C(CH₃)=C(=N-N=)O-C-CCl₃ | 97.5-100 | 295 | 2.26 |
| 14 | 4-CH₃O-C₆H₄-CH=CH-C(=N-N=)O-C-CH₂Cl | 139-141 | 323 | 3.22 |
| 15 | 4-CH₃O-C₆H₄-CH=CH-C(=N-N=)O-C-CF₃ | 117-118 | 326 | 2.45 |
| 16 | 4-CH₃O-C₆H₄-C(C₆H₅)=C(=N-N=)O-C-CCl₃ | 129-131 | 337 | 1.56 |
| 17 | 4-CH₃O-C₆H₄-CH=CH-C(=N-N=)O-C-CBr₃ | 160-161 | 336 | 3.24 |
| 18 | 3,4-methylenedioxy-C₆H₃-CH=CH-C(=N-N=)O-C-CBr₃ | 161-163 | 349 | 2.79 |

| Compound | Structural Formula | m.p. (°C.) | MeOH λMax | ε × 10$^{-4}$ |
|---|---|---|---|---|
| 19 | 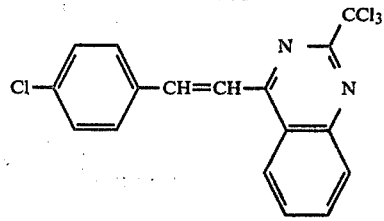 | 167–169 | 319 | 3.19 |

Of these compounds, Compounds Nos. 1, 5, 7, 9, 10, 11 12 and 17 are preferred and Compounds Nos. 1, 5, 7, 9 and 10 are most preferred.

Compounds of general formula (I) in accordance with the present invention are essentially different in structure from the vinyl-halomethyl-s-triazine compounds described in U.S. Pat. Nos. 3,954,475 (J. A. Bonham et al), and 3,987,037.

That is, in the compounds of the present invention, conjugated bonds connecting halomethyl group to aromatic ring are represented by the following general formula:

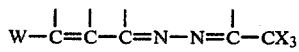

whereas in the compounds of Bonham et al, they are represented by the following general formulae:

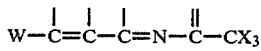

and

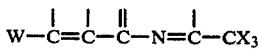

Further, the compounds of the present invention are analogous to the compounds of Bonham et al in that the halomethyl group is bound to a light-absorbing group. However, it is not correct to conclude, for this reason, that the compounds of the present invention would be obvious from the compounds of Bonham et al, because, compounds of the following formulae, for example, have almost no free radical-generating ability when exposed to light though a halomethyl group is bound to a light-absorbing group.

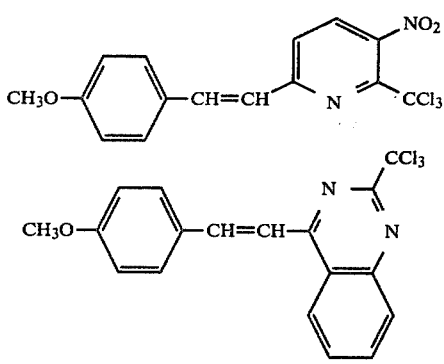

When irradiated with actinic light of about 300 to about 500 nm in wavelength, the 1,3,4-oxadiazole compounds of the present invention produce free radicals. Thus, the compounds are useful as photo reaction initiators to be used in light-sensitive compositions and light-sensitive elements. These can be compounded in photopolymerizable compositions and printing compositions for use in producing printing plates such as lithographic, typographic or intaglio printing plates or compounded in light-sensitive resist-forming compositions capable of providing visible images by merely exposing to light.

The free radical-generating agents of the present invention are particularly useful as photo-initiators for a photosensitive composition for producing lithographic printing plates, IC circuits or photomasks. They enable one to form visible images through exposure to light without development in a light-sensitive resist-forming composition. Such light-sensitive resist compositions enable one to obtain images visible under a yellow safety lamp for exposing work by only exposure. Therefore, in the steps of exposing many printing plates at the same time, it is possible to know whether plates given to the plate-making workers have been exposed or not in the case of, for example, work being interrupted.

Similarly, in the case of exposing a large plate many times as in so-called photo composing step and repeat printing down process for preparing lithographic printing plates, workers can immediately confirm areas already exposed.

The light-sensitive resist-forming composition capable of immediately providing visible images upon exposure in which the free radical-generating agent of the present invention can be advantageously used is usually made up of a light-sensitive resist-forming compound, free radical-generating agent and color-changing agent as necessary ingredients and, optionally, one or more of plasticizer, binding agent, dye other than color-changing agent, pigment, anti-fogging agent, sensitizing agent for light-sensitive resist-forming compound, etc.

Suitable amount of the free radical-generating agent of this invention used in the light-sensitive resist-forming composition is 0.01 to 100 parts by weight per 100 parts by weight of the light-sensitive resist-forming compound in the composition.

The present invention will now be illustrated in more detail by reference to following Examples which, however, do not limit the present invention in any way.

EXAMPLE 1

Synthesis of 2-Trichloromethyl-5-(p-methoxystyryl)-1,3,4-oxadiazole (Compound No. 7)

17.8 g of p-methoxycinnamic acid and 13.9 g of p-nitrophenol were heated for an hour under reflux in 50 ml of thionyl chloride and 50 ml of benzene. Excess thionyl chloride and benzene were distilled off, and the resulting solid was washed with water, then dried. Thus, there was obtained p'-nitrophenyl p-methoxycinnamate in a substantially theoretical amount.

18.0 g of p'-nitrophenyl p-methoxycinnamate was added to 11.4 g of 80% hydrazine hydrate and 75 ml of methanol, followed by heating for 30 minutes under reflux. After cooling the reaction solution, 6.3 g of triethylamine was added thereto, and the mixture was poured into 400 ml of water. Thus, there were precipitated 7.9 g of colorless crystals of p-methoxycinnamic acid hydrazide.

19.2 g of p-methoxycinnamic acid hydrazide was added to 29.2 g of hexachloroacetone and 100 ml of acetonitrile, and heated for 20 minutes under reflux. Upon cooling the reaction solution, there were precipitated 30.1 g of colorless crystals of N-p-methoxycinnamoyl-N'-trichloroacetyl hydrazide.

4 g of N-p-methoxycinnamoyl-N'-trichloroacetyl hydrazide and 40 ml of phosphorus oxychloride were heated for 3 hours under reflux, and then poured into 200 g of ice water. Precipitates thus-formed were recrystallized from methanol to obtain 2.5 g of 2-trichloromethyl-5-(p-methoxystyryl)-1,3,4-oxadiazole (m.p.: 140.5°–141.5° C.).

The resulting compound was subjected to elemental analysis, and NMR in $CDCl_3$, mass spectrum, ultraviolet ray absorption spectrum, and IR absorption spectrum were measured.

Elemental Analysis

|  | H | C | N |
| --- | --- | --- | --- |
| Found (%): | 3.04 | 44.94 | 8.80 |
| Calcd. (%): | 2.84 | 45.10 | 8.77 |

NMR (measured at 60 MHz in $CDCl_3$ using TMS as a standard material)

S values:
3.80 (S, 3)
6.74 (d, 1, J=15.5 Hz)
6.84 (d, 2, J=7.5 Hz)
7.43 (d, 2, J=7.5 Hz)
7.58 (d, 1, J=15.5 Hz)

Results of mass spectrum: (Ion-accelerating voltage: 6 kv; ionization potential: 70 eV; ionization current: 150 μA; sample heating temperature: 70°–80° C.; ion source temperature: 190° C.)

| m/e | Intensity | m/e | Intensity |
| --- | --- | --- | --- |
| 62 | 5.5 | 162 | 8.6 |
| 74 | 4.5 | 178 | 3.3 |
| 75 | 5.5 | 201 | 3.6 |
| 89 | 9.3 | 282 | 16.0 |
| 90 | 6.7 | 283 | 25.0 |
| 102 | 10.2 | 284 | 12.0 |
| 103 | 4.3 | 285 | 19.0 |
| 116 | 7.1 | 317 | 100.0 |
| 118 | 5.5 | 318 | 32.0 |
| 133 | 16.0 | 319 | 92.0 |
| 143 | 5.7 | 320 | 28.0 |
| 144 | 4.0 | 321 | 29.0 |
| 145 | 4.8 | 322 | 9.6 |
| 159 | 26.0 | 323 | 5.6 |
| 161 | 72.0 | | |

Results of IR absorption spectrum (measured according to KBr Nujor method)

Positions of peaks: 2900, 2810, 1630, 1595, 1570, 1515, 1450, 1430, 1415, 1360, 1300, 1290, 1255, 1240, 1200, 1170, 1105, 1025, 990, 960, 840, 830, 810, 795, 775, 675, 545, 515 $cm^{-1}$.

EXAMPLE 2

Synthesis of 2-Trichloromethyl-5-(3',4'-methylenedioxystyryl)-1,3,4-oxadiazole (Compound No. 11)

The above-identified compound was obtained by using 3,4-methylenedioxycinnamic acid instead of p-methoxycinnamic acid in the same manner as in Example 1.

Melting point of this compound was 156°–158° C., and results of elemental analysis are as described below.

Elemental Analysis

|  | H | C | N |
| --- | --- | --- | --- |
| Found (%): | 2.26 | 43.46 | 8.45 |
| Calcd. (%): | 2.12 | 43.21 | 8.40 |

EXAMPLE 3

Synthesis of 2-Chloromethyl-5-(p-methoxystyryl)-1,3,4-oxadiazole (Compound No. 14)

1.9 g of p-methoxycinnamic acid hydrazide, the intermediate obtained in Example 1, was stirred for 30 minutes at room temperature in a mixture of 1.7 g of monochloroacetic acid anhydride and 15 ml of acetic acid. Then, the mixture was poured into water, and the thus-obtained precipitates were recrystallized from a mixed solvent of methanol and water to obtain 0.8 g of N-p-methoxycinnamoyl-N'-chloroacetylhydrazide.

0.8 g of N-p-methoxycinnamoyl-N'-chloroacetylhydrazide and 10 ml of phosphorus oxychloride were heated for 1 hour under reflux, and the reaction solution was poured into ice-water. The precipitates thus-formed were recrystallized from ethanol to obtain 0.4 g of 2-chloromethyl-5-(p-methoxystyryl)-1,3,4-oxadiazole (m.p.: 139°–141° C.).

Results of the elemental analysis of this compound are as follows.

|  | H | C | N |
| --- | --- | --- | --- |
| Found (%): | 4.53 | 57.68 | 10.93 |
| Calcd. (%): | 4.39 | 57.49 | 11.18 |

EXAMPLE 4

Synthesis of 2-Trifluoromethyl-5-(p-methoxystyryl)-1,3,4-oxadiazole (Compound No. 15)

3.8 g of p-methoxycinnamic acid hydrazide, the intermediate obtained in Example 1, was dissolved in 20 ml of glacial acetic acid, and 4.2 g of trifluoroacetic acid anhydride was added thereto under stirring. White precipitates formed were collected by filtration, and recrystallized from aqueous ethanol to obtain 3.2 g of N-p-methoxycinnamoyl-N'-trifluoroacetyl-hydrazine.

1 g of N-p-methoxycinnamoyl-N'-trifluoroacetylhydrazide and 10 ml of phosphorus oxychloride were heated for 5 hours under reflux, and the reaction solution was poured into ice-water. Precipitates thus-formed were recrystallized from ethanol to obtain 0.4 g of 2-trifluoromethyl-5-(p-methoxystyryl)-1,3,4-oxadiazole. m.p.: 117°–118° C.

Elemental Analysis

|  | H | C | N |
|---|---|---|---|
| Calcd. (%): | 3.36 | 53.34 | 10.37 |
| Found (%): | 3.58 | 53.51 | 10.53 |

EXAMPLE 5

Synthesis of 2-Tribromomethyl-5-(p-methoxystyryl)-1,3,4-oxadiazole (Compound No. 17)

8.75 g of p-methoxycinnamic acid hydrazide, the intermediate obtained in Example 1, was dissolved in 180 ml of dioxane, and 8.2 g of tribromoacetic acid bromide was dropwise added thereto in 10 minutes under stirring. The reaction solution was stirred for 4 hours at room temperature, and the resulting precipitates were filtered out. After adding 200 ml of water to the filtrate, the mixture was cooled to obtain 8.8 g of the crystals of N-p-methoxycinnamoyl-N'-tribromoacetyl-hydrazide.

3.9 g of the crystals and 20 ml of phosphorus oxychloride were heated for 1 hour under reflux, then the reaction solution was poured into ice-water. Precipitates thus-formed were recrystallized from ethyl acetate to obtain 2.0 g of 2-tribromomethyl-5-(p-methoxystyryl)-1,3,4-oxadiazole. m.p.: 160°–161° C.

Elemental Analysis

|  | H | C | N |
|---|---|---|---|
| Calcd. (%): | 2.00 | 31.82 | 6.18 |
| Found (%): | 2.06 | 32.11 | 6.23 |

In order to show the usefulness of the compounds of the present invention, the experiments of the following examples were conducted.

EXAMPLE 6

Production of Positive Type Presensitized Lithographic Printing Plates

On 0.15 mm-thick aluminum plate (1) having been surface-grained was coated the following light-sensitive composition using a whirler, and dried for 2 minutes at 100° C. to obtain light-sensitive lithographic printing plates.

| | |
|---|---|
| Esterification product of naphthoquinone-(1,2)-diazide (2)-5-sulfonyl chloride and pyrogallol acetone resin (prepared as in Example 1 of U.S. Pat. No. 3,635,709) | 0.75 g |
| Cresol novolak resin | 2.1 g |
| Tetrahydrophthalic acid anhydride | 0.15 g |
| Crystal Violet | 0.02 g |
| Free radical-generating agent (shown in Table 2) | 0.03 g |
| Ethylene dichloride | 18 g |
| Methyl Cellosolve | 12 g |

The coated amount after drying was 2.2 g/m$^2$.

Each of these presensitized lithographic printing plates was exposed to a 30 A carbon arc lamp spaced at a distance of 70 cm, and developed at 25° C. for 60 seconds using an aqueous 5 wt% sodium silicate (molar ratio of SiO$_2$/Na$_2$O:1.74) solution to measure the sensitivity. Proper exposure time was selected so that 5th step in gray scale of 0.15 in optical density difference between steps was completely clear.

Optical densities of the light-sensitive layers in exposed areas and unexposed areas with time were measured using Macbeth densitometer.

Further, after incubating these light-sensitive lithographic printing plates, the above-described measurement was repeated. Incubation conditions were 45° C. in temperature, 75% in humidity and 7 days in period.

Images obtained by exposure appear more distinct as the difference between the density of exposed areas and that of unexposed areas (ΔD) increases.

TABLE 2

Properties of Presensitized Lithographic Printing Plates

| Run No. | Free Radical-Generating Agent | Resist[1] Sensitivity (second) | Optical Density (D) of Light-Sensitive Layer | | | | | |
|---|---|---|---|---|---|---|---|---|
| | | | 1 Day After Coating | | | After Incubation (at 45° C. and 75% for 7 days) | | |
| | | | Unexposed Area | Exposed Area | ΔD | Unexposed Area | Exposed Area | ΔD |
| 1 | — | 65 | 0.89 | 0.89 | 0.00 | 0.89 | 0.89 | 0.00 |
| 2* | Compound No. 7 | 68 | 0.89 | 0.75 | 0.14 | 0.89 | 0.76 | 0.13 |
| 3** | 2,4-Bis(trichloromethyl)-6-(p-methoxystyryl)-s-triazine | 75 | 0.87 | 0.71 | 0.16 | 0.86 | 0.72 | 0.14 |
| 4** | Naphthoquinone-1,2-diazido-(2)-4-sulfonylchloride | 66 | 0.88 | 0.78 | 0.10 | 0.87 | 0.82 | 0.05 |
| 5** | 2-Trichloromethyl-3-nitro-6-(p- | 68 | 0.89 | 0.89 | 0.00 | 0.89 | 0.89 | 0.00 |

TABLE 2-continued

Properties of Presensitized Lithographic Printing Plates

| | | | Optical Density (D) of Light-Sensitive Layer | | | | | |
|---|---|---|---|---|---|---|---|---|
| | | Resist[1] | 1 Day After Coating | | | After Incubation (at 45° C. and 75% for 7 days) | | |
| Run No. | Free Radical-Generating Agent | Sensitivity (second) | Unexposed Area | Exposed Area | ΔD | Unexposed Area | Exposed Area | ΔD |
| | methoxystyryl)-pyridine | | | | | | | |
| 6** | 2-Trichloromethyl-4-(p-methoxystyryl)-quinazoline | 69 | 0.88 | 0.88 | 0.00 | 0.88 | 0.88 | 0.00 |

[1]Proper exposure time for forming resist image (resist sensitivity)
*Present invention
**Comparative Example The greater ΔD, the more distinct the image.

From Table 2, it is seen that free radical-generating agent, Compound No. 7, of the present invention is excellent in incubation resistance as compared with naphthoquinone-1,2-diazido-(2)-4-sulfonylchloride, a conventional free radical-generating agent. Also, 2,4-bis(trichloromethyl)-6-p-methoxystyryl-s-triazine is inferior in that it reduces resist sensitivity, though it shows the same good incubation resistance as that of free radical-generating agent No. 7 of the present invention. Further, 2-trichloromethyl-3-nitro-6-(p-methoxystyryl)pyridine or 2-trichloromethyl-4-(p-methoxystyryl)quinazoline do not possess the ability of changing the density of exposed areas by exposure.

EXAMPLE 7

Process for Producing a Positive Type Light-Sensitive Lithographic Printing Plate On 0.24 mm-thick aluminum plate (II) having been surface-grained and subjected to anodic oxidation was coated the following light-sensitive solution to obtain a light-sensitive lithographic printing plate.

| | |
|---|---|
| Esterification product of naphthoquinone-(1,2)-diazido-(2)-5-sulfonylchloride and poly-p-hydroxystyrene (m.w.: 7,000) | 0.70 g |
| Cresol novolak resin | 2.25 g |
| p-tert-Butylphenol novolak resin | 0.05 g |
| Tetrahydrophthalic acid anhydride | 0.15 g |
| Compound No. 11 | 0.02 g |
| Oil Blue #603 C. I. 74350 | 0.02 g |
| Tetrahydrofuran | 18 g |
| Methyl Cellosolve acetate | 12 g |

A distinct print-out image was obtained by imagewise exposing this plate without development.

EXAMPLE 8

Process for Producing a Negative Type Light-Sensitive Lithographic Printing Plate On aluminum plate (II) used in Example 7 was coated the following light-sensitive solution using a whirler.

| | |
|---|---|
| Esterification product of polyvinyl alcohol (saponification degree: 88%; polymerization degree: 1,000) and p-azidobenzoic acid | 0.5 g |
| 1-Nitro-4-acetaminonaphthalene | 0.02 g |
| Compound No. 3 | 0.008 g |
| Leuco Crystal Violet | 0.008 g |
| Dioctyl phthalate | 0.1 g |
| Ethylene dichloride | 6 g |

| | |
|---|---|
| -continued | |
| Monochlorobenzene | 9 g |

A print-out image with high contrast was obtained by imagewise exposing this light-sensitive lithographic printing plate.

While the invention has been described in detail and with reference to specific embodiments thereof, it will be apparent to one skilled in the art that various changes and modifications can be made therein without departing from the spirit and scope thereof.

What is claimed is:

1. Compounds represented by the following general formula (I):

$$W-CH=C-C \underset{X}{\overset{N=N}{\underset{\|}{\|}}} C-CY_3 \quad (I)$$

wherein W represents a phenyl group, a phenyl group substituted with a member selected from the group consisting of a halogen atom, a nitro group, a cyano group, an alkyl group containing 1 to 3 carbon atoms and an alkoxy group containing 1 to 4 carbon atoms, with the number of the substituents being 1 or 2 when said substituent is a halogen atom and 1 when said substituent other than a halogen atom, or an unsubstituted naphthyl group and said phenyl group may take the form of $$H_2C\underset{O}{\overset{O}{\diagdown}}\text{—benzene ring}$$

X represents a hydrogen atom, an unsubstituted phenyl group or an alkyl group containing 1 to 3 carbon atoms, and Y represents a halogen atom.

2. The compounds of claim 1, wherein W represents an unsubstituted or substituted phenyl group.

3. The compounds of claim 2, wherein X represents a hydrogen atom.

4. The compounds of claim 2, wherein said substituent is an alkoxy group.

5. The compounds of claim 1, wherein W represents (a) an unsubstituted phenyl group, (b) a phenyl group substituted with one chlorine atom or an alkoxy group having 1 to 4 carbon atoms or (c) a group represented by the following formula:

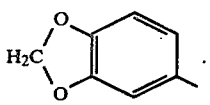

6. The compounds of claim 4, wherein said substituent on said phenyl group is a methoxy group.

7. The compounds of claim 4, wherein said substituent on said phenyl group is a cyano group.

8. The compounds of claim 1, wherein said compound is

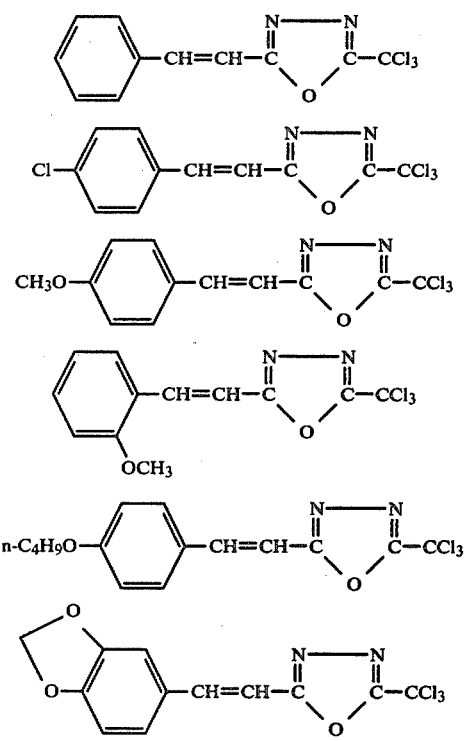

-continued

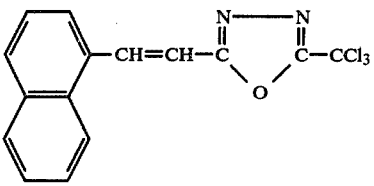

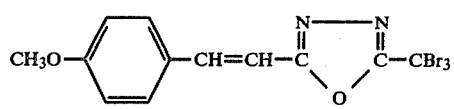

9. The compounds of claim 1, wherein said compound is

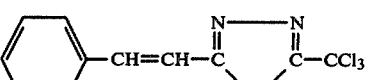

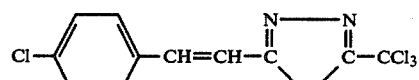

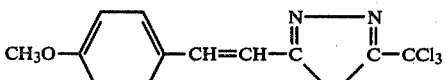

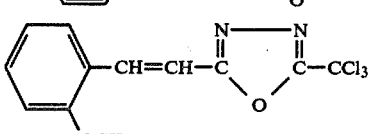

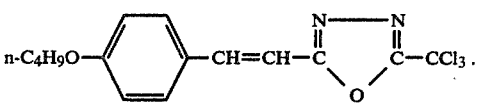

10. The compounds of claim 1, wherein Y represents a chlorine atom, a bromine atom or a fluorine atom.

11. The compounds of claim 1, wherein Y represents a chlorine atom or a bromine atom.

* * * * *